(12) United States Patent
Lu

(10) Patent No.: US 6,334,071 B1
(45) Date of Patent: Dec. 25, 2001

(54) MINUTE VOLUME PACEMAKERS THAT REQUIRE ONLY A SINGLE DISTAL ELECTRODE

(75) Inventor: Richard Lu, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/326,939

(22) Filed: Jun. 7, 1999

(51) Int. Cl.[7] ................................................. A61N 1/365
(52) U.S. Cl. ........................................................ 607/20
(58) Field of Search .............................. 607/18, 20, 24, 607/36; 600/547

(56) References Cited

U.S. PATENT DOCUMENTS

| | | | |
|---|---|---|---|
| 4,702,253 | 10/1987 | Nappholz et al. | 128/419 |
| 4,712,555 | 12/1987 | Thornander et al. | 128/419 |
| 4,788,980 | 12/1988 | Mann et al. | 128/419 |
| 4,809,697 | 3/1989 | Causey et al. | 128/419 |
| 4,901,725 | 2/1990 | Nappholz et al. | 128/419 |
| 4,940,052 | 7/1990 | Mann et al. | 128/419 |
| 4,944,298 | 7/1990 | Sholder | 128/419 |
| 4,944,299 | 7/1990 | Silvian | 128/419 |
| 5,562,712 | 10/1996 | Steinhaus et al. | 607/20 |
| 5,824,020 | 10/1998 | Cooper | 607/17 |
| 5,876,353 | * 3/1999 | Riff | 600/547 |
| 5,957,861 | * 9/1999 | Combs et al. | 607/547 |
| 6,055,454 | * 4/2000 | Heemels | 607/18 |
| 6,080,187 | * 6/2000 | Alt et al. | 607/32 |

* cited by examiner

Primary Examiner—Jeffrey R. Jastrzab

(57) ABSTRACT

In a rate-responsive pacemaker, the metabolic demand of the patient is determined by measuring the patient's minute volume. Preferably, the pacemaker has a housing with a header, two external electrodes formed on the housing and/or the header, and at least one lead with a distal electrode extending from the header to the patient's heart. The minute volume is determined by injecting a test current pulse between one of the external electrodes and the distal electrode, and detecting the resulting voltage between the distal electrode and the second external electrode.

20 Claims, 3 Drawing Sheets

MINUTE VOLUME PACEMAKERS THAT REQUIRE ONLY A SINGLE DISTAL ELECTRODE

FIELD OF THE INVENTION

This invention pertains to implantable devices providing cardiac therapy to a patient, and more particularly to pacemakers adapted to provide pacing on demand in single- or dual-chamber modes for patients suffering from bradycardia (pacing rates lower than the sinus rhythm). Frequently, such devices are also incorporated into implantable cardioversion devices (ICDs) used to treat tachyarrhythmias. More particularly, the present invention pertains to pacemakers which provide pacing on demand using a metabolic demand parameter such as minute volume to determine the optimal pacing rate.

Minute volume (MV, sometimes referred to as minute ventilation) has become accepted in the industry as a metabolic demand parameter because it is indicative of the respiration rate and tidal volume of the patient.

BACKGROUND OF THE INVENTION

Prior to the present invention, minute volume has been typically measured using three electrodes, with two of the electrodes being in the same cardiac chamber (i.e., either the atrium or the ventricle), and the third electrode being at the end of a lead or comprising the pacemaker case. A current was passed between one of the electrodes in the cardiac chamber and the third electrode. The resulting voltage between the other electrode in the cardiac chamber and the third electrode was measured. The current and the voltage values were then used to determine the transthoracic impedance dynamically. (See, for instance, U.S. Pat. No. 4,702,253.) A problem with this approach is that it requires at least two electrodes disposed within the heart. As a result, MV type pacemakers could not be implanted to replace old pacemakers using a unipolar lead (with only one electrode), or a bipolar lead one of whose wires is broken (thus also having only one effective electrode).

U.S. Pat. No. 4,901,725 shows how to determine minute volume using standard bipolar leads, each bipolar lead consisting of a ring and a tip electrode. In this patent, current is injected between the ring electrode and the pacemaker case. The voltage between the tip electrode and the case is used to determine the transthoracic impedance.

U.S. Pat. No. 5,562,712 teaches how to measure MV using two unipolar leads, the two leads terminating at electrodes in different cardiac chambers. This configuration is useful when an MV pacemaker replaces a standard pacemaker coupled to two unipolar leads, rather than a bipolar lead.

Of course, a major disadvantage of all these arrangements is that they still require at least two electrodes in the heart of the patient. In the prior art, an MV pacemaker could not be used to replace a pacemaker used with a unipolar lead, or used with a multi-wire lead in which only one wire is still intact.

SUMMARY OF THE INVENTION

In general terms, the subject application pertains to a rate-responsive pacemaker using MV as the metabolic indicating parameter, and which requires only a single distal electrode, such as the electrode of a unipolar lead, to measure the MV parameter. Preferably, the pacemaker measures the MV parameter by providing two electrodes on the case of the pacemaker, and using the distal electrode of the lead as the common return. In this manner, current can be injected between one of the case electrodes and the distal electrode, and what is sensed is the resulting voltage between the second case electrode and the distal electrode. In one configuration, the case is provided with two dot electrodes. In another configuration, all or most of the surface of the pacemaker case is used as one of the case electrodes, and a dot electrode (insulated electrically from the rest of the case) is used as the other case electrode.

A pacemaker constructed in accordance with this invention includes a case having two electrodes, with a lead coupled to (but insulted from) the case having a distal electrode in a cardiac chamber. The case and the distal electrode are arranged so that they span the pleural cavity of the patient.

The pacemaker includes a sensing amplifier for sensing intrinsic cardiac activity, a timing and control circuit coupled to the sensing amplifier which generates trigger signals, and a pace generator that generates pacing pulses in response to the trigger signals.

Importantly, the pacemaker further includes a metabolic demand sensor circuit for sensing the metabolic demand of the patient. The timing and control circuit, which is based on a microprocessor, is coupled to the metabolic demand sensor circuit so that it can operate in a rate-responsive mode.

The metabolic demand sensor circuit includes a current source arranged to inject a current between one of the case electrodes and the distal electrode. The metabolic demand sensor circuit further includes a voltage monitor circuit that monitors the resulting voltage between the second case electrode and the distal electrode. This voltage is used as a measure of the transthoracic impedance.

BRIEF DESCRIPTION OF THE DRAWINGS AND APPENDIX

The above and other aspects, features and advantages of the present invention will be more apparent from the following more particular description thereof, presented in conjunction with the following drawings and appendix wherein.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

As indicated above, the present invention may be used with various types of implantable medical devices, including an implantable cardioverter-defibrillator (ICD) or an implantable single-chamber or dual-chamber pacemaker.

Figure 1:
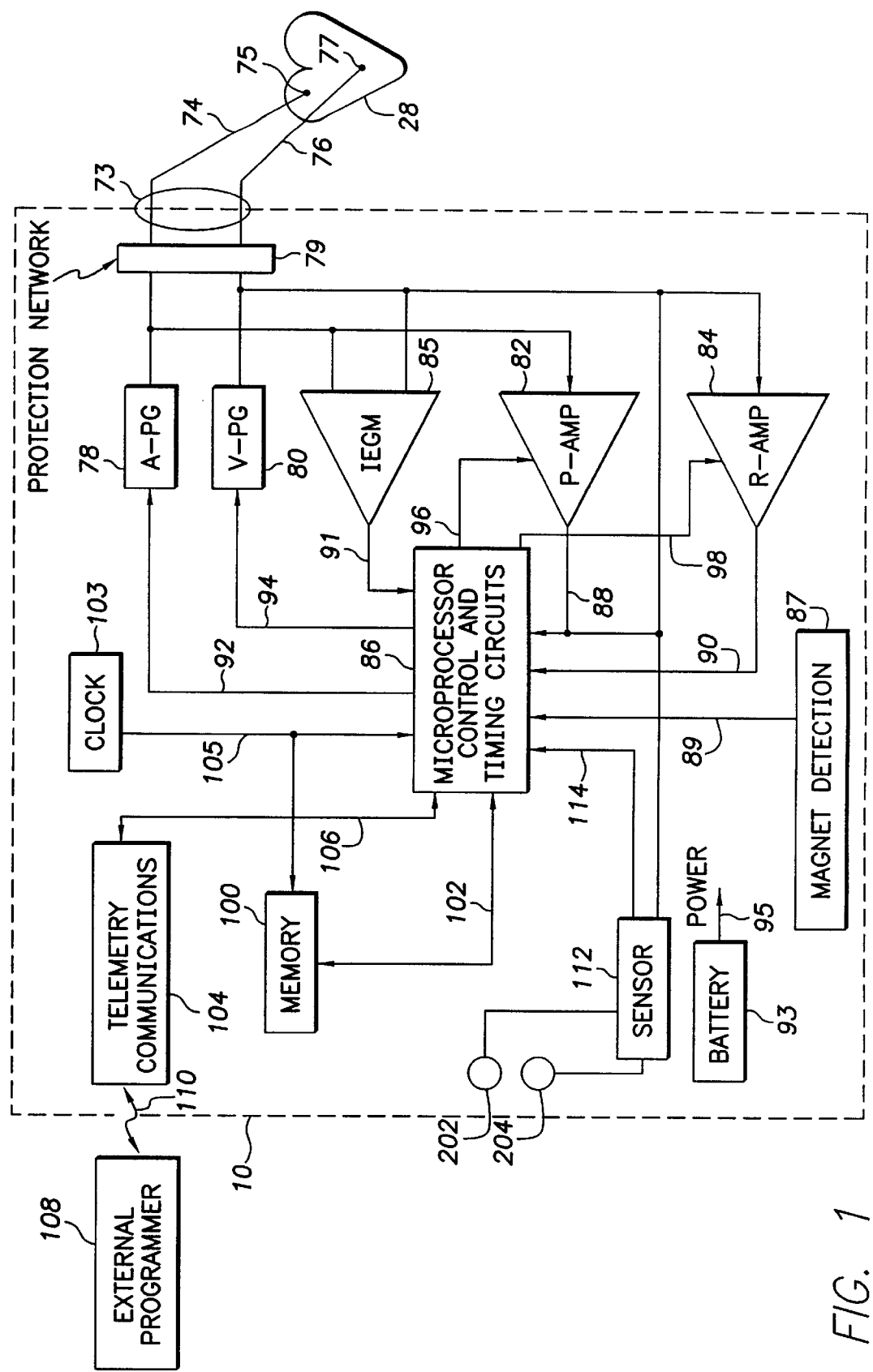
FIG. 1 is a functional block diagram of an implantable, programmable, dual-chamber pacemaker, in accordance with the present invention.

FIG. 1, a simplified block diagram of a dual-chamber pacemaker 10, is illustrated as a separate system for the sake of simplicity, it being understood that the pacemaker may be combined with or incorporated into an ICD. The pacemaker 10 is coupled to a heart 28 by leads 74 and 76. The leads are electrically and physically connected to the pacemaker 10 through a connector 73 that forms an integral part of the housing containing the pacemaker circuits.

Leads 74 and 76 terminate respectively in the atrium and the ventricle, and could be either unipolar or bipolar leads. If leads 74 and 76 are unipolar, they each have a single wire (not shown) and terminate with a single electrode, 75 and 77, respectively. If leads 74 and 76 are bipolar, then each lead has two wires and terminates with two electrodes, such as a tip and a ring electrode. For this latter 5 configuration, the tip and ring electrodes terminating lead 74 are jointly identified and referred to herein by numeral 75 and the tip and ring electrodes terminating lead 76 are identified and referred to herein by numeral 77. (The invention requires use of only a single one of the electrodes, on only one lead.)

The connector 73 is electrically connected to a protection network 79 which electrically protects the circuits within the pacemaker 10 from excessive shocks or voltages that could appear on the distal electrodes 75 and/or 77 in the event such electrodes were to be subjected to a high voltage signal, e.g., from a defibrillator shock.

The leads 74 and 76 carry stimulating pulses to the distal electrodes 75 and 77 from an atrial pulse generator (A-PG) 78 and a ventricular pulse generator (V-PG) 80, respectively. Further, electrical signals from the atria indicative of atrial intrinsic activity flow from the distal electrode 75, through the lead 74, to the input of an atrial channel sense amplifier (P-AMP) 82; and electrical signals from the ventricles indicative of ventricular intrinsic activity flow from the distal electrode 77, through the lead 76, to the input of a ventricular channel sense amplifier (R-AMP) 84. Similarly, electrical signals from both the atria and ventricles are applied to the inputs of an IEGM (intracardiac electrogram) amplifier 85. The IEGM amplifier 85 is typically configured to detect an evoked response from the heart 28 in response to an applied stimulus, thereby aiding in the detection of "capture". (Capture occurs when an electrical stimulus applied to the heart is of sufficient energy to depolarize the cardiac tissue, thereby causing the heart muscle to contract, or, in other words, causing the heart to beat. Capture does not occur when an electrical stimulus applied to the heart is of insufficient energy to depolarize the cardiac tissue.)

The dual-chamber pacemaker 10 is controlled by a control system 86 that typically includes a microprocessor programmed to carry out control and timing functions. The control system 86 receives output signals from the atrial channel sense amplifier (P-AMP) 82 over signal line 88. Similarly, the control system 86 receives output signals from the ventricular channel sense amplifier (R-AMP) 84 over signal line 90, and output signals from the IEGM amplifier 85 over signal line 91. These output signals are generated each time that a P-wave or an R-wave or an evoked response is sensed within the heart 28.

The control system 86 generates trigger signals that are delivered to the atrial pulse generator (A-PG) 78 and the ventricular pulse generator (V-PG) 80 over signal lines 92 and 94, respectively. These trigger signals are generated each time that a stimulation pulse is to be generated by the respective atrial or ventricular pulse generator 78 or 80. The atrial trigger signal is referred to simply as the "A-trigger", and the ventricular trigger signal is referred to simply as the "V-trigger". During the time that either an atrial pulse or a ventricular pulse is being delivered to the heart, the amplifiers P-AMP 82 and R-AMP 84 are typically disabled by way of blanking signals presented to these amplifiers from the control system 86 over signal lines 96 and 98, respectively. This blanking action prevents the amplifiers 82 and 84 from becoming saturated from the relatively large stimulation pulses that are present at their inputs during this time. This blanking action also helps prevent residual electrical signals present in the muscle tissue as a result of the pacemaker stimulation from being interpreted as P-waves or R-waves.

Still referring to FIG. 1, the pacemaker 10 also includes a memory circuit 100 that is coupled to the control system 86 over a suitable data/address bus 102. This memory circuit 100 allows certain control parameters, used by the control system 86 in controlling the operation of the pacemaker 10, to be programmably stored and modified, as required, in order to customize the pacemaker operation to suit the needs of a particular patient. Further, data sensed during the operation of the pacemaker may be stored in the memory circuit 100 for later retrieval and analysis.

The memory circuit 100 may take many forms, and may be subdivided into as many different memory blocks or sections (addresses) as needed in order to allow desired data and control information to be stored.

The operating mode of the dual-chamber pacemaker 10 may be dependent, at least in part, on past performance data. For example, an average atrial rate may be determined based on the sensed atrial rate over a prescribed period of time. This average rate may then be stored and updated at regular intervals. Such stored rate may then be compared to a present atrial rate, and the difference used to control the operating mode of the pacemaker. Other parameters, of course, in addition to (or in lieu of) atrial rate, may be similarly sensed, stored, averaged or otherwise processed, and then used for comparison purposes against one or more currently-sensed parameter. Advantageously, modern memory devices allow for the storage of large amounts of data in this manner.

A clock circuit 103 directs an appropriate clock signal to the control system 86, as well as to any other circuits needing clock pulses (e.g., to the memory circuit 100) by way of clock bus 105.

A telemetry communications circuit 104 is further included in the pacemaker 10. This telemetry communications circuit 104 is connected to the control system 86 by way of a suitable command/data bus 106. In turn, the telemetry communications circuit 104, which is included within the implantable pacemaker 10, may be selectively coupled to an external programming device 108 by means of an appropriate communication link 110, which communications link may be any suitable electromagnetic link, such as an RF (radio frequency) channel, a magnetic link, an inductive link, an optical link, and the like. Advantageously, through the external programming device 108 and the communications link 110, desired commands may be sent to the control system 86. Similarly, through this communications link with the external programming device 108, data (either held within the control system 86, as in a data latch, or stored within the memory circuit 100) may be received from the external programming device 108. Similarly, data initially sensed through the leads 74 or 76, and processed by the control system 86, or other data measured within or by the dual-chamber pacemaker, may be stored and uploaded to the external programming device 108. In this manner, non-invasive communications can be established with the implanted pacemaker 10 from a remote location.

The pacemaker 10 additionally includes a battery 93 which provides operating power to all of the circuits of the pacemaker via a POWER signal line 95.

It is noted that the dual-chamber pacemaker 10 in FIG. 1 is referred to as a dual-chamber pacemaker because it interfaces with both the atria and the ventricles of the heart. Those portions of the dual-chamber pacemaker that interface with the atria, e.g., the lead 74, the atrial channel sense amplifier (P-AMP) 82, the atrial pulse generator (A-PG) 78, and corresponding portions of the control system 86, are commonly referred to as the "atrial channel". Similarly, those portions of the dual-chamber pacemaker that interface with the ventricles, e.g., the lead 76, the ventricular channel sense amplifier R-AMP) 84, the ventricular pulse generator (V-PG) 80, and corresponding portions of the control system 86, are commonly referred to as the "ventricular channel".

Importantly, the pacemaker 10 may further include at least one sensor 112 that is connected to the control system 86 over a suitable line 114. Details of this sensor 112 are discussed more fully below. The sensor 112 is capable of sensing a physiological parameter related to the rate at which the heart should be beating (i.e., related to the metabolic demand of the patient), and/or related to whether a tachyarrhythmia is likely to soon occur. Such sensors are commonly used with "rate-responsive" pacemakers in order to adjust the rate (pacing cycle) of the pacemaker in a manner that tracks the physiological or metabolic needs of the patient.

The pacemaker 10 may further include magnet detection circuitry 87, coupled to the control system 86 over signal line 89. It is the purpose of the magnet detection circuitry 87 to detect when a magnet is placed over the pacemaker, which magnet may be used by a physician or other medical personnel to perform various reset functions of the pacemaker, and/or to signal the control system 86 that an external programming device 108 is in place to receive data from, or send data to, the pacemaker memory circuit 100 or control system 86 through the telemetry communications circuit 104.

The telemetry communications circuit 104 may be of conventional design, such as is described in U.S. Pat. No. 4,944,299, or as is otherwise known in the art. Similarly, the external programming device 108 may be of any suitable design known in the art, such as is described in U.S. Pat. No. 4,809,697. Likewise, the memory circuit 100, and the circuits utilized in the atrial and ventricular channels may all be of common design, as is known in the pacing art. The present invention is not concerned with the details of the circuitry utilized for each of these pacemaker elements. Rather, it is concerned with the manner in which all of these elements cooperate with each other in order to provide a particular mode of operation.

The control system 86 may be realized by using a variety of different techniques and/or circuits. The preferred type of control system 86 is a microprocessor-based control system. It is noted, however, that the control system 86 could also be realized using a state machine. Indeed, any type of control circuit or system could be employed for the control system 86. The present invention is likewise not concerned with the details of the control system 86. Rather, it is concerned with the end result achieved by the control system. That is, so long as the control system 86 controls the operation of the pacemaker (or other medical device), it matters little what type of control system is used. Those of skill in the implantable medical device art, given the teachings presented herein, should thus be able to fashion numerous different types of control systems or circuits that achieve the desired device control.

Representative of the types of control systems that may be used with the invention is the microprocessor-based control system described in U.S. Pat. No. 4,940,052, entitled "Microprocessor Controlled Rate-Responsive Pacemaker Having Automatic Rate Response Threshold Adjustment". Reference is also made to U.S. Pat. Nos. 4,712,555 and 4,944,298, wherein a state-machine type of operation for a pacemaker is described, and U.S. Pat. No. 4,788,980, wherein the various timing intervals used within a pacemaker and their inter-relationships are more thoroughly described. The '052, '555, '298 and '980 patents are incorporated herein by reference.

The present invention is directed to a rate-responsive device wherein the sensor 112 senses minute volume as the metabolic demand parameter. More specifically, the sensor 112 is coupled to two electrodes 202, 204 disposed on the external housing or case of the pacemaker 10, as well as a distal electrode, such as (but not limited to) distal electrode 77 disposed in the ventricle at the end of lead 76.

Figure 2:
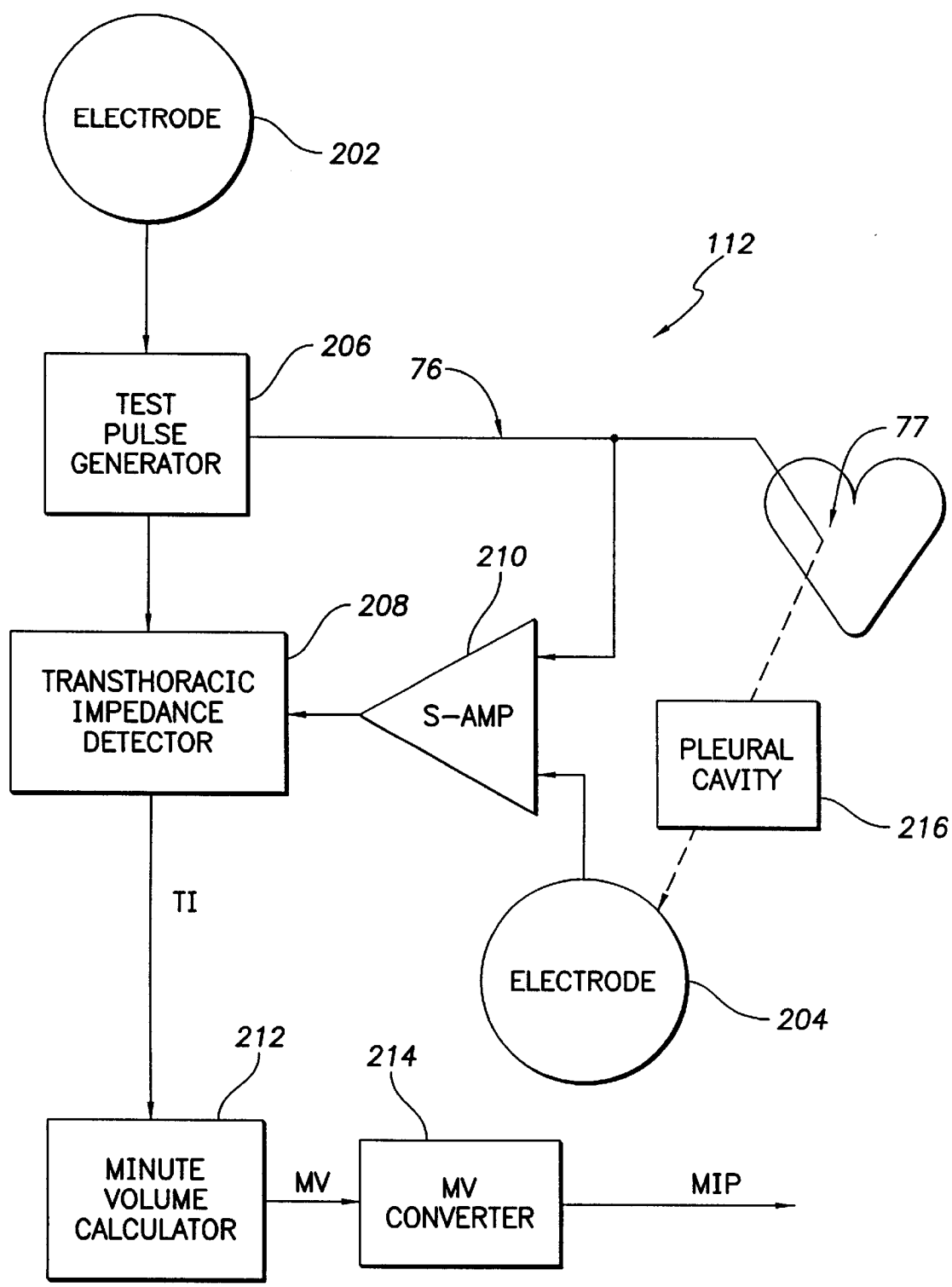
FIG. 2 is a block diagram of the metabolic demand sensor 112 of FIG. 1.

Referring now to FIG. 2, sensor 112 includes a test pulse generator 206, a transthoracic impedance detector 208, a sense amplifier (S-AMP) 210, a minute volume calculator 212, and an MV converter 214.

At regular intervals, the test pulse generator 206 generates a test current pulse having a predetermined amplitude and duration. This test current pulse is transmitted over lead 76 and distal electrode 77 into the respective cardiac chamber, which in this case is a ventricle, and returns through the electrode 202. A corresponding voltage signal induced by this current is detected between electrode 204 and the distal electrode 77, and amplified by amplifier (S-AMP) 210. For proper rate control based on the transthoracic impedance, preferably the injected current and sensed voltage should be across the pleural cavity 216. The amplified signal from amplifier (S-AMP) 210 is fed to a transthoracic impedance detector 208 which then generates a parameter TI proportional to the respective transthoracic impedance. The parameter TI is fed to a minute volume calculator 212 which calculates minute volume changes from a base value thereby determining a parameter MV. Parameter MV is fed to MV-converter 214 which converts the parameter MV into a metabolic demand indicated parameter MIP. The general principles relating to determining minute volume and how the minute volume and MIP are used in a rate-responsive pacemaker are described in commonly owned U.S. Pat. No. 4,901,725 to Nappholz et al., and U.S. Pat. No. 5,824,020 to Cooper. The control and timing circuits 86 use this parameter MIP to determine the hemodynamically optimal pacing rate for the patient.

Figure 3:
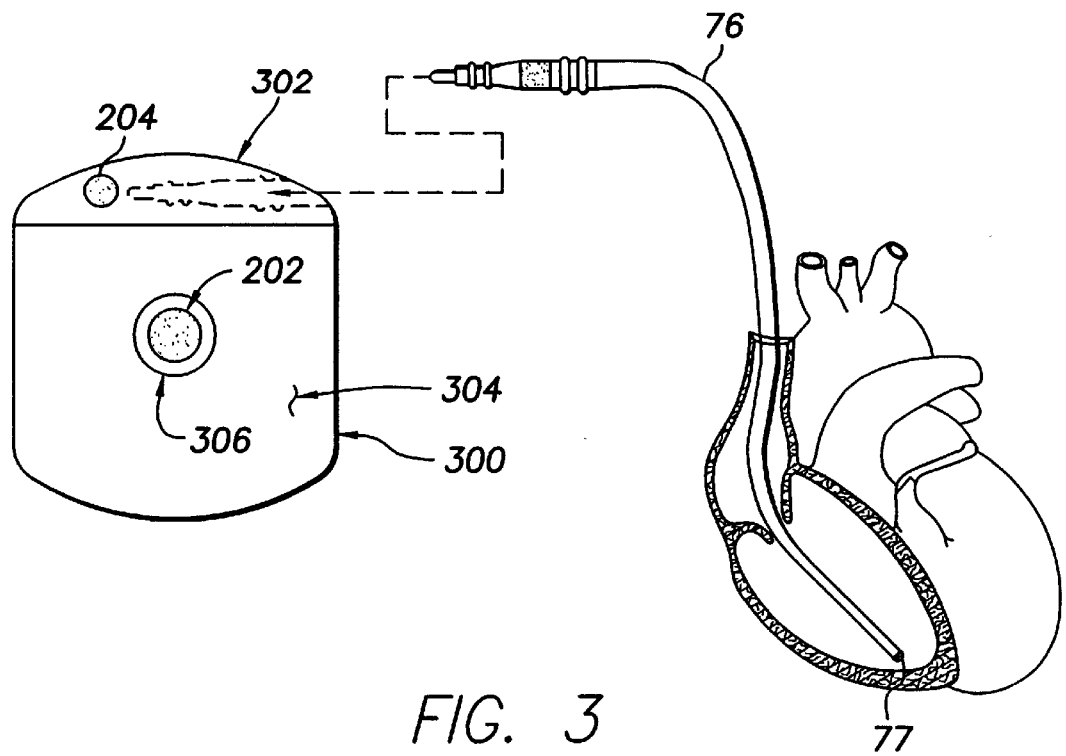
FIG. 3 is a somewhat diagrammatic elevational view of a pacemaker case and an associated unipolar lead.

Referring now to FIG. 3, the dual-chamber pacemaker 10 includes a hermetically sealed case or housing 300 generally made of a metallic material and having a header 302. Lead 76 is attached to the header 302 in the usual manner (shown only diagrammatically). Importantly, the case 300 is also provided with the two external dot electrodes 202, 204. Preferably, electrode 202 is disposed on a major surface 304 of case 300 and is isolated therefrom by an insulating ring 306. Dot electrode 204 is formed on the header 302 as shown. Both dot electrodes are connected to circuitry within the case by standard-type feedthroughs.

Several other alternative arrangements may also be used for the subject invention. For example, if the case or housing is used as a common return electrode, then dot electrode 202 may be omitted. Alternatively, when the case is used as an electrode together with dot electrode 202, the dot electrode 204 on the header may be omitted.

Figure 4:
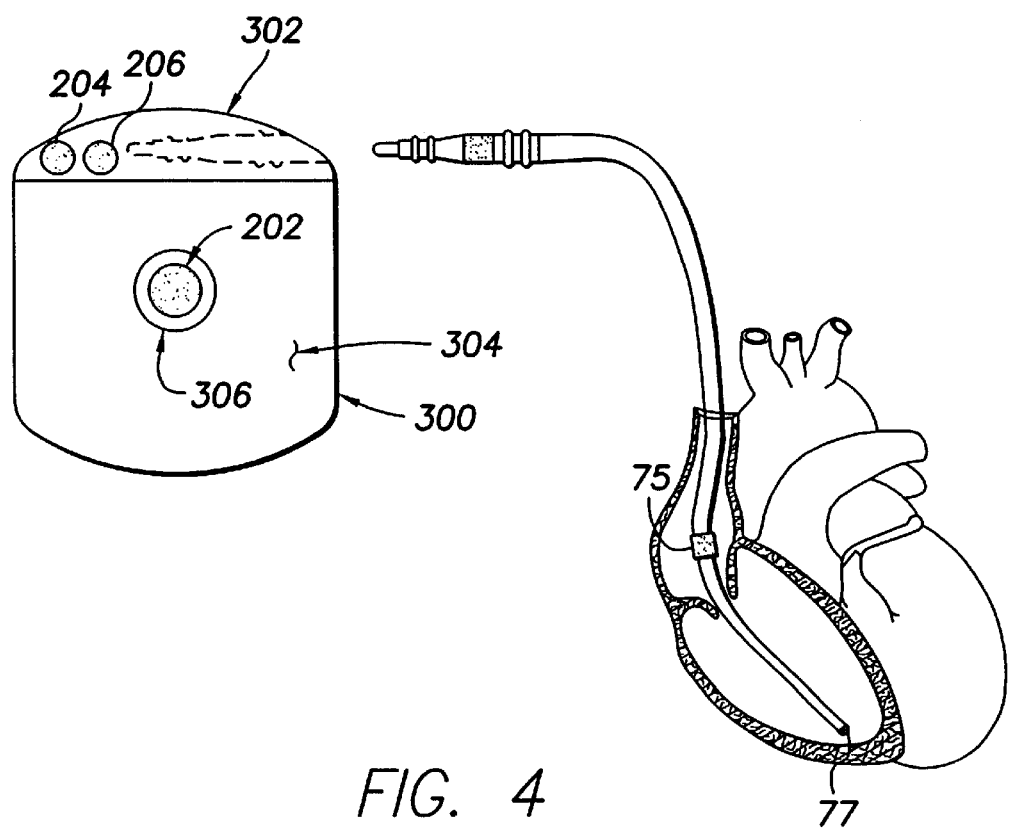
FIG. 4 shows the pacemaker case of FIG. 2 with two-dot electrodes on the header.

Another arrangement shown in FIG. 4 is to use dot electrodes 204 and 206 on the header without using the case for MV measurements. In such case, the function of the case in the MV measurement process is provided by dot electrode 206 in a manner similar to that described for the case.

In addition, instead of using a distal electrode 77 in the ventricle, the distal electrode 75 in the atrium (or in the ventricle or a coil electrode) could be used. Similarly with the pacemaker stimulator of an ICD, one of the defibrillator electrodes may be used to determine minute volume by the process described above.

For example, if lead 76 is a bipolar lead, and one of the wires, such as the wire connecting to the tip electrode is broken, the pacemaker 10 is still capable of determining the minute volume by using the ring electrode, since the wire to the ring electrode is still intact.

In this manner, a pacemaker may operate in a rate-responsive mode and determine the metabolic demand of the patient by using only a single distal electrode. This distal electrode may be associated with a unipolar lead or be one electrode of a bipolar lead. While the invention has been described by means of specific embodiments, it is understood that modifications and variations could be made thereto by those skilled in the art without departing from the spirit and the scope of the invention. It is therefore to be understood that within the scope of the claims, the invention may be practiced otherwise than as specifically described herein.

What is claimed is:

1. An implantable cardiac stimulator comprising:
   a housing having two external electrodes formed thereon;
   a unipolar lead electrically isolated from the housing but extending therefrom and terminating at a distal electrode adapted for location in the heart of a patient;
   a pulse generator disposed within the housing and generating stimulation pulses on the lead in response to trigger signals;
   a metabolic demand detector that detects the metabolic demand of the patient and generates a metabolic demand parameter, the metabolic demand detector including a test pulse generator that generates a test pulse between one of the two external electrodes and the distal electrode, and a test sensor that senses voltage developed in response to the test pulse between the second of the two external electrodes and the distal electrode, the metabolic demand parameter being dependent on the sensed voltage; and
   a control and timing circuit that generates the trigger signals at a rate determined by the magnitude of the metabolic demand parameter.

2. The stimulator of claim 1, wherein the distal electrode is adapted to be disposed in a cardiac chamber, and the pulse generator generates pacing pulses, the pacing pulses being extended to the cardiac chamber through the distal electrode.

3. The stimulator of claim 2, wherein the distal electrode is disposed in an atrium.

4. The stimulator of claim 2, wherein the distal electrode is disposed in a ventricle.

5. The stimulator of claim 1, further comprising a sense amplifier coupled to the distal electrode for sensing intrinsic activity in a patient's heart, the sense amplifier generating a sense signal, and wherein the control and timing circuit responds to the sense signal as well as the magnitude of the metabolic demand parameter.

6. The stimulator of claim 1, wherein the external electrodes are dot electrodes formed on the housing.

7. The stimulator of claim 1, wherein the housing includes a housing body forming one of the external electrodes and a header attached to the housing body from which the lead extends.

8. The stimulator of claim 7, wherein the other of the external electrodes comprises a dot electrode.

9. The stimulator of claim 8, wherein the dot electrode is disposed on the header.

10. The stimulator claim 8, wherein the dot electrode is on the housing body but is electrically isolated therefrom.

11. The pacemaker of claim 1, wherein the housing comprises a metallic body and a header coupled to the housing body, with the lead extending from the header, wherein the first and second external electrodes are located on the header.

12. A rate-responsive pacemaker comprising:
    a housing having first and second external electrodes formed thereon;
    a unipolar lead electrically isolated from the housing but extending therefrom and having a distal electrode adapted to be disposed in a cardiac chamber;
    a sensor amplifier that senses intrinsic activity in a patient's heart and generates a corresponding sense signal;
    a metabolic demand sensor in the housing for generating a current pulse between the distal electrode and the first housing external electrode and for sensing the voltage corresponding to the current pulse between the distal electrode and the second housing external electrode, the voltage being indicative of the metabolic demand of the patient;
    a control and timing circuit responsive to the sense signal and the voltage for generating trigger signals; and
    a pulse generator disposed in the housing for generating cardiac stimulation pulses in response to the trigger signals.

13. The pacemaker of claim 12, wherein the first and second external electrodes are dot electrodes formed on the housing.

14. The pacemaker of claim 12, wherein the housing comprises a metallic body that constitutes one of the first and second external electrodes, and a header coupled to the housing body, with the lead extending from the header.

15. The pacemaker of claim 12, wherein the other of the first and second external electrodes is on the header.

16. The pacemaker of claim 15, wherein the other of the first and second electrodes is a dot electrode.

17. The pacemaker of claim 14, wherein the other of the first and second electrodes is a dot electrode formed on the housing and electrically insulated from the metallic body.

18. The pacemaker of claim 12, wherein the housing comprises a metallic body and a header coupled to the housing body, with the lead extending from the header, wherein the first and second external electrodes are located on the header.

19. A method of providing rate-responsive stimulation to a patient's heart using an implantable stimulator having a housing formed with two external electrodes thereon and a unipolar lead extending from the housing to the patient's heart and including a distal electrode, comprising the steps of:

sensing an intrinsic activity within the heart and generating a corresponding sense signal;

determining the metabolic demand of the patient by generating a test pulse between one of the external electrodes and the distal electrode and detecting a response signal corresponding to the test pulse between the other of the external electrodes and the distal electrode;

generating a metabolic demand parameter corresponding to the response signal; and generating pacing pulses responsive to the metabolic demand and the sense signal.

20. The method of claim 19, wherein the step of determining the metabolic demand of the patient includes generating a current test pulse and detecting a voltage constituting the metabolic response signal.

* * * * *